US007393834B2

(12) United States Patent
Bouchard et al.

(10) Patent No.: US 7,393,834 B2
(45) Date of Patent: *Jul. 1, 2008

(54) LHRH-ANTAGONISTS IN THE TREATMENT OF FERTILITY DISORDERS

(75) Inventors: Philippe Bouchard, Paris (FR); Rene Frydman, Paris (FR); Paul Devroey, Aalst (BE); Klaus Diedrich, Gross Sarau (DE); Jurgen Engel, Alzenau (DE)

(73) Assignee: AEterna Zentaris GmbH, Frankfurt (DE)

( * ) Notice: Subject to any disclaimer, the term of this patent is extended or adjusted under 35 U.S.C. 154(b) by 245 days.

This patent is subject to a terminal disclaimer.

(21) Appl. No.: 10/661,780

(22) Filed: Sep. 15, 2003

(65) Prior Publication Data

US 2005/0049200 A1 Mar. 3, 2005

Related U.S. Application Data

(63) Continuation of application No. 09/053,152, filed on Apr. 1, 1998, now abandoned, which is a continuation-in-part of application No. 08/786,937, filed on Jan. 22, 1997, now abandoned.

(60) Provisional application No. 60/011,282, filed on Feb. 7, 1996.

(51) Int. Cl.
A61K 38/09 (2006.01)
A61K 31/551 (2006.01)
A61K 31/4743 (2006.01)

(52) U.S. Cl. ............................. 514/16; 514/14; 514/15; 514/215

(58) Field of Classification Search ....................... 514/2, 514/15, 16, 215; 530/313, 328, 329, 312
See application file for complete search history.

(56) References Cited

U.S. PATENT DOCUMENTS

| 6,022,860 | A | 2/2000 | Engel et al. | |
| 6,077,523 | A | 6/2000 | Deghenghi | |
| 6,319,192 | B1 * | 11/2001 | Engel et al. | 600/33 |

FOREIGN PATENT DOCUMENTS

| WO | WO 9955357 A1 * | 11/1999 |
| WO | WO 200059542 A1 * | 10/2000 |

OTHER PUBLICATIONS

"Will GnRH antagonists provide new hope for patients considered 'difficult responders' to GnRH agonist protocols!", Craft et al., Human Reproduction, vol. 14, No. 12, pp. 2959-2962, 1999.*
"Use of cetrorelix in combination with clomiphene citrate and gonadotrophins: a suitable approch to friendly IVF?", Engel et al., Human Reproduction, vol. 17, No. 8, pp. 2022-2026, 2002.*
"Ovarian stimulation by clomiphene citrate and hMG in combination with cetrorelix acetate for ICSI cycles", Hwang et al., Human Reproduction, vol. 18, No. 1, pp. 45-49, 2003.*
"Gonadotropin-releasing hormone anatagonist protocol:a novel method of ovarian stimulation in poor responders", Nikolettos et al., European Journal of Obstetrics & Gynecology and Reproductive Biology, 97 (2001) 202-207.*
Klingmuller et al., "Hormonal responses to the new potent GnRH antagonist Cetrorelix," Acta Endocrinologica, 128:15-18, Jan. 1993.
Albano et al., "Hormonal Profile During the Follicular Phase in Cycles Stimulated with a Combination of Human Menopausal Gonadotrophin and Gonadotrophin-Releasing Hormone Antagonist (Cetrorelix)," Human Reproduction, vol. 11, No. 10, pp. 2114-2118, 1996.
Awonuga et al., "In vitro Fertilization with Low-Dose Clomiphene Citrate Stimulation in Women Who Respond Poorly to Superovulation," Journal of Assist Reprod. Genetics, vol. 14, No. 9, pp. 503-507; Oct. 1997.
Diedrich et al., "Suppression of the Endogenous Luteinizing Hormone Surge by the Gonadotrophin-Releasing Hormone Antagonist Cetrorelix During Ovarian Stimulation," Human Reproduction, vol. 9, No. 5, pp. 788-791, May 1994.
Felberbaum et al., Eur. J. Obstet. Gynecol. Reprod. Biol., vol. 61, No. 2, pp. 151-515, 1995.
Felberbaum et al., "Hormone Profiles and Pituitary Response Under Ovarian Stimulation With HMG and GnRH Antagonists (Cetrorelix)," Human Reproduction, vol. 9, No. 4, p. 13, 1994.
Jennings et al., "In Vitro fertilisation. A Review of Drug Therapy and Clinical Management," Drugs, vol. 52, No. 3, pp. 313-343, Sep. 1996.
Leroy et al., "A Single Injection of a Gonadotropin-Releasing Hormone (GnRH) Antagonist (Cetrorelix)* Postpones the Luteinizing Hormone (LH) Surge: Further Evidence for the Role of GnRH During the LH Surge," Fertility and Sterility, vol. 62, No. 3, pp. 461-467, Sep. 1994.

(Continued)

Primary Examiner—Brian-Yong S Kwon
(74) Attorney, Agent, or Firm—Pillsbury Winthrop Shaw Pittman LLP

(57) ABSTRACT

A method of treating infertility disorders by 1) administering an LH-RH antagonist, preferably Cetrorelix, in amounts to selectively suppress endogenous LH but not FSH secretion and 2) inducing follicle growth by administration of exogenous gonadotropin. The selective suppression OF LH allows FSH secretion to be at natural levelS thereby not affecting individual estrogen development. The LH-RH antagonist can be given as a single or dual subcutaneous dose in the range of 1 mg to 10 mg, preferably 2 mg-6 mg. In multiple dosing-posology, LH-RH antagonist can be administered subcutaneously in an amount in the range of 0.1 to 0.5 mg of LH-RH antagonist/day. LH-RH antagonist is applied starting cycle day 1 to 10, preferably on day 4 to 8, and ovulation can be induced between day 9 and 20 of the menstruation cycle by administering rec. LH, native LH-RH, LH-RH agonist or by HCG. In addition rec. LH, native LH-RH or LH-RH agonist can be given to avoid hyperstimulation syndrome and native LH-RH or a LH-RH agonist can be administered to avoid luteal phase stimulation by neutralizing the negative effects of HCG.

21 Claims, 1 Drawing Sheet

OTHER PUBLICATIONS

Olivennes et al., "Scheduled Administration of a Gonadotrophin-Releasing Hormone Antagonist (Cetrorelix) on Day 8 of In-Vitro Fertilization Cycles: A Pilot Study," *Human Reproduction*, vol. 10, No. 6, pp. 1382-1386, Jun. 1995.

Olivennes et al., "The Single or Dual Administration of the Gonadotropin-Releasing Hormone Antagonist Cetrorelix* in an In Vitro Fertilization-Embryo Transfer Program," *Fertility and Sterility*, vol. 62, No. 3, pp. 468-476, Sep. 1994.

Reissmann et al., "Development and Applications of Luteinizing Hormone-Releasing Hormone Antagonists in the Treatment of Infertility: An Overview," *Human Reproduction*, vol. 10, No. 8, pp. 1974-1981, 1995.

Nestor, Jr. et al., "Potent gonadotropin releasing hormone antagonists with low histamine-releasing activity," J. Med. Chem., Institute of Bio-Organic Chemistry, vol. 35 (No. 21), p. 3942-3948, (Oct. 16, 1992).

Deghenghi et al., "Antarelix (EP 24332) a novel water soluble LHRH antagonist," Biomed. Pharmacother., Europeptides (Argenteuil, France), vol. 47 (No. 2-3), p. 107-110, (1993).

Rivier et al., "Gonadotropin-releasing hormone antagonists with N omega-triazolylomithine, -lysine, or -p-aminophenylalanine residues at positions 5 and 6," J. Med. Chem., Salk Institute for Biological Studies (La Jolla, California), vol. 35 (No. 23), p. 4270-4278, (Nov. 13, 1992).

Haviv et al., "In vitro and in vivo activities of reduced-size antagonists of luteinizing hormone-releasing hormone," J. Med. Chem., TAP Pharmaceuticals, Inc. (Abbott Park, IL), vol. 37 (No. 5), p. 701-705, (Mar. 4, 1994).

Weinbauer et al., "Comparison of the antigonadotropic activity of three GnRH antagonists (Nal-Glu, Antide and Cetrorelix) in a non-human primate model (Macaca fascicularis),"Andrologia, Institute of Reproductive Medicine of the University (Munster, Germany), vol. 25, (No. 3), p. 141-147, (May-Jun. 1993).

* cited by examiner

LHRH-ANTAGONISTS IN THE TREATMENT OF FERTILITY DISORDERS

CROSS REFERENCE TO RELATED APPLICATIONS

This is a continuation of U.S. patent application No. 09/053,152, filed Apr. 1, 1998, now abandoned, which is a continuation-in-part of U.S. patent application No. 08/786,937, filed Jan. 22, 1997, which claims priority to U.S. Provisional Patent Application No. 60/011,282, filed Feb. 7, 1996, the contents of each of which are incorporated herein by reference.

FIELD OF THE INVENTION

The field of invention is directed to the use of LHRH-antagonists to treat male and female fertility disorders.

BACKGROUND OF THE INVENTION

The reasons for unsuccessful attempts to establish pregnancy can be attributed equally to male and female fertility disorders. Today many different assisted reproduction techniques are available. These techniques are used to induce multiple and synchronous follicular growth and thereby obtain fertilizable oocytes.

The current standard treatment is to induce multiple follicular development by administering high doses of HMG (Human Menopausal Gonadotropin). This results in ovarian hyperstimulation. Upon reaching a suitable degree of oocyte maturation using these techniques, ovulation is induced by the administration of HCG (Human Chorionic-Gonadotropin) in order to obtain a sufficient number of oocytes. During this time, the clinic-infrastructure preparation can begin. Preparation includes recovery of oocytes by abdominal or transvaginal puncture, intracorporal or extracorporal fertilization of oocytes by different techniques and embryo replacement into the uterus. Routinely, beginning pregnancy is supported by additional administrations of HCG or progesterone. Today this treatment is applied to clinical conditions of male and female infertility.

Complications that are frequently observed during the hyperstimulation procedure are:

A: premature surges of luteinizing hormone (LH) at a premature maturation state with a rupture of the follicles that induced a subsequent cancellation of the treatment occurring in about 25% of the patients; and B: ovarian hyperstimulation syndromes induced by exogenous gonadotropins which in severe cases require hospitalization and are life-threatening.

In order to avoid premature LH-surges, today LHRH-agonists are used as a comedication. By continued administration of these drugs, a complete suppression of endogenous gonadotropins is achieved by desensitization of pituitary cells and down-regulation of their receptors. Subsequently, the gonadotropin levels can be controlled by exogenous injection and the pituitary is refractory to the stimulation of LH-release by increasing levels of estradiol. Disadvantages are 1) a long treatment period until the suppression and down-regulation occur; 2) estrogen withdrawal symptoms; 3) disturbance of the normal menstrual cycle; 4) the need for frequent hormone determinations in order to evaluate the time of onset of suppression; and 5) high dose HMG treatment is needed for ovarian stimulation.

The pathogenesis of hyperstimulation syndrome is not completely understood, but is thought to be associated with the use of HCG for ovulation induction and luteal phase support.

One recent approach involves the use of the LHRH antagonist Cetrorelix (INN). In first clinical trials, short term treatment with Cetrorelix resulted in a complete avoidance of premature LH surges during stimulated cycles and the need for HMG. Due to the immediate suppression of gonadotropins by this antagonist, the unwanted stimulatory phase and also the withdrawal of estrogen produced by the agonists was avoided. The duration of treatment was also significantly shortened. In addition, it was shown that a single injection of an antagonist, given in the mid-follicular phase, would adequately suppress premature LH surges.

SUMMARY OF THE INVENTION

Despite the improvements described above, these treatment modalities suffered the drawback of treating the patients with the highest possible dose of exogenous gonadotropins to hyperstimulate multiple follicular development which results in some severe adverse events.

The current invention reduces the severe adverse events, improves patient compliance and reduces costs. Recent data obtained with Cetrorelix also demonstrates additional surprising new advantages for the treatment of male and female infertility.

In animal experiments and clinical studies with Cetrorelix, it was possible to induce an arrest of the normal, unstimulated follicular growth by multiple or single injections. These effects were observed with extremely low dosage levels. These low dosage levels present new possibilities for manipulating the time of ovulation during a normal, not exogenous gonadotropin-stimulated cycle, without affecting the viability of the growing follicle. In case of inadequate follicular growth related to treatment with LHRH-antagonists, low dose and short term administration of gonadotrophin or other trophic compounds will compensate for these effects. Subsequently, by stopping the LHRH-antagonist treatment, it is possible to let the normal ovulation occur or to induce ovulation by exogenous manipulation, if necessary. Ovulation induction was induced by the administration of standard HCG or by administration of LHRH and/or LHRH agonistic analogs.

These described treatment alternatives are a departure from existing protocols, since they are possible only if preceded by treatment for LH-surge-control with an LHRH-antagonist. In animal and clinical studies with Cetrorelix it was shown that the responsiveness of the pituitary to LHRH or agonistic analogs is preserved under these conditions of treatment. Without this treatment, the pituitary cannot respond after agonistic pretreatment for LH-surge control due to receptor down-regulation. In addition, the possible use of ovulation inducing agents other than HCG results in a-reduced incidence of ovarian hyperstimulation syndrome.

On the basis of the described results, for the first time it is possible to use normal, non-gonadotropin-stimulated cycles for assisted reproduction techniques, including sperm injections, by determining the time of ovulation by the duration and dose of Cetrorelix given. Especially in conjunction with the method of ICSI (Intra-Cytoplasmatic-Sperm-Injection) this antagonist-dependent treatment modality facilitates the inclusion of in-(sub-)fertile males into this kind of fertility treatment. Due to the direct injection of male gametes capable for fertilization, this method has a high success rate and hence, allows the harvest of only one follicle for fertilization. In addition, the use of LHRH-antagonists like Cetrorelix in the described manner relieves the patient from severe ovarian hyperstimulation and significantly reduces the costs of a treatment cycle.

LHRH-antagonists of the invention can be used in combination with assisted reproduction techniques, especially the extracorporal fertilization, e.g. the in-vitro fertilization and the sperm injection techniques.

as convenient as a single or dual injection. On the other hand, regular monitoring of the hormones is not required and the application of HCG could even be extended if required in rare cases.

In summary, from a medical point of view, both treatments show comparable efficacy, safety and practicability, therefore each gynecologist should have the possibility to decide upon the dosing schedule with respect to the situation observed in each single patient.

The results of a phase II clinical trial are shown in Table I. A total of 235 patients were treated.

No premature LH surge was seen in any patient undergoing COS/ART treated with either multiple doses of 0.25 mg or higher or a single dose of 3 mg or higher. During multiple dosing, the mean days of Cetrorelix application is 6 days. 25 babies were born by the end of May 1996 (7 following multiple doses; 18 following single/dual doses).

TABLE I

Cetrorelix Development Controlled Ovarian Stimulation (COS/ART)

| Subj. Nos. | Phase | Dose/Day (mg) | Posology (days) |
|---|---|---|---|
| 14 | II/proof concept | 3 | 3-10 |
| 19 | II/proof concept | 1 | 3-10 |
| 11 | II/proof concept | 0.5 | 3-10 |
| 32 | II/ | 0.5 | 3-7/14 |
| 30 | dose finding/ | 0.25 min. effect. dose | |
| (28) | minimal effective dose | 0.10 no effect. dose | |
| 21 | II/proof concept | 5 | 1 or 2 |
| 18 | II/proof concept | 3 | 1 or 2 |
| 32 | II/dose finding/ | 3 min. effective dose | 1 |
| 30 | minimal effective dose | 2 no effect. Dose | 1 |
| SUM Phase II | 235 finished | 71 pregnancies (30%) 16 pregnancies (ongoing) | 44 healthy children |

Compounds with the desired LHRH-antagonistic activity include a LHRH-analog such as Ganirelix, Antarelix, Antide, Azaline B, Ramorelix, A-76154, Nal-Glu, 88-88, in particular Cetrorelix or a structure-truncated peptide with LHRH-antagonistic activity or a peptideomimetic with LHRH-antagonistic activity, for example D-23980 and D-24824, or a bicyclic (1-4. 4-10) LHRH analog with antagonistic activity.

LHRH-antagonists of the invention can be subcutaneously administered in dosage amounts of about 0.001-0.2 mg/kg.

Both dosing schedules demonstrate the prevention of any premature LH surge. After both posologies good fertilization rates have been obtained with good follicle and oocytes quality. Pregnancy rates are good after both treatments. To date, a total of 44 healthy babies have been born following both treatments.

The single dose regimen requires only one single injection of 3 ml. This has to be regarded as being convenient for the patient. So far, duration of effect to prevent a premature LH surge is up to 6.5 days. After 3 days, monitoring of hormones is advisable in order to apply a second injection in case of a low responder to HMG with prolonged administration of HMG, and if an increase of LH values is seen.

The multiple dose schedule requires daily injections of 1 ml for 3 to 7 days, sometimes up to 10 or 14 days. This is not The main advantages in controlled ovarian stimulation (COS/ART) with Cetrorelix are:
1. New therapeutic principle
    a) Prevention of premature LH-surges
    b) Uniform and continuous follicular synchronization
    c) Uniform and continuous estradiol development
    d) Very low LH-values for optimal follicular development
2. Short term treatment of 3 to 7 days to max 14 days
    a) Short-term exposure during follicular development
    b) Low medication exposure during follicular development
3. No flare-up but immediate hormonal response
4. No pretreatment for 14 to 21 days before start of HMG needed
5. Fits well into normal menstrual cycle with
    a) No modification of physiological menstrual cycle pattern or
    b) No hormonal withdrawal syndromes before stimulation
6. No or only ultrashort-term residual effects after ovulation induction
7. No residual effects during and following embryo transfer
8. No ovarian cyst formation before start of stimulation
9. Reduction of HMG.

Table II (flow chart) shows an example on a typical treatment start and duration of HMG and Cetrorelix in patients to undergo controlled ovarian superovulation for ART.

TABLE II

Summary of assessments (Flow-chart)

| Treatment/ Investigations | pre | hMG day 1[1] Cycle day 2 or 3 | hMG days d2-d5 | hMG day d6 (Cetrorelix) | hMG day[2] D7 until the day of hCG (Cetrorelix) | hCG[4] apply if: lead follicle: ≧20 mm φ or $E_2$ ≧ 1,200 pg/ml Parameters: cancel, if: ≧12 foll. ≧ 15 mmφ or $E_2$ ≧ 4,000 pg/ml (≧14,684 pmol/l) | OPU | ET | 6-8 days after ET | Final Docum.: Day 20-25 after ET | POST hMG PERIOD |
|---|---|---|---|---|---|---|---|---|---|---|---|
| Screening data End of Trial Form | X | | | | | | | | | X[6] | Pregnancy and Baby follow up Follow-up: replacement cycles |
| Cetrorelix 0.25 mg s.c. daily | | | | X | X | X | | | | | |
| hMG inj. (2/3/4+) | | X[1] 2 Amp | X 2 Amp | X 2+++ Amp | X[2] 2+++ Amp | X[2] 2+++ Amp | | | | | |
| → hCG 10,000 IU i.m. injection | | | | | | X[3] | | | | | |
| Ultrasound (USS) | X | X | | (X) optional | (X) optional | X | X | | | X | |
| Hormones: (hCG) LH, FSH, $E_2$, P | X | X[1] | | X | X daily | X[7] 2-times: morning + just before hCG | X | X | X | X | |
| Lab (Hemat. clin. chem.) | X | | | X | | | x | | X | | |
| Luteal phase support → hCG or Progesterone | | | | | | | | X[5] | X[5] | | |
| Tolerability/ AE's | X | | | < ... at every visit ... > | | | | | | | |

$X^1$ = 1st day (d 1) of hMG injection: after confirmation (verified in the morning) of: menstrual bleeding; no pregnancy: hCG → neg. (≦10 IU/l): P ≦ 1 ng/ml (≦3.81 nmol/l); FSH ≦ 10 IU/l; no ovarian cyst (≧2 cm φ producing $E_2$ ≧ 50 pg/ml (≧185 pmol/l)).
d1 of hMG = day 2 or 3 of menstrual cycle !
$X^2$ = last day of hMG administration depends on follicle maturation (see $X^3$).
$X^3$ = day of injection of 10,000 IU hCG: as soon as at least 1 follicle with a mean diameter of 20 mm, measured by ultrasound (USS) or $E_2$ ≧ 1 200 pg/ml (≧4 405 pmol/l), is observed.
$X^4$ = CAVE: In case of >12 follicles ≧ 15 mm φ or $E_2$ ≧ 4 000 pg/ml (≧14 684 pmol/l) during stimulation period → no hCG injection ! → Cycle cancellation !
$X^5$ = Luteal phase support according to centre's rule: Either injections of hCG according to centre's rule or vagin. application of Progesterone (e.g. 3× 200 mg/day) will be given accord. to centre's rule. !
$X^6$ = Must always be documented in any case of any premature study termination (e.g. in case of any Drop out).
$X^7$ = Blood samples for hormone determination on the day of hCG will be withdrawn 2 times (morning and just before hCG application) at hospital or out-site.
Ultrasound (USS): (X) will be undertaken according to centre's rule between day 6 of hMG until the day of HCG! USS has to be performed on the day of HCG!

EXAMPLE 1

Figure 1:
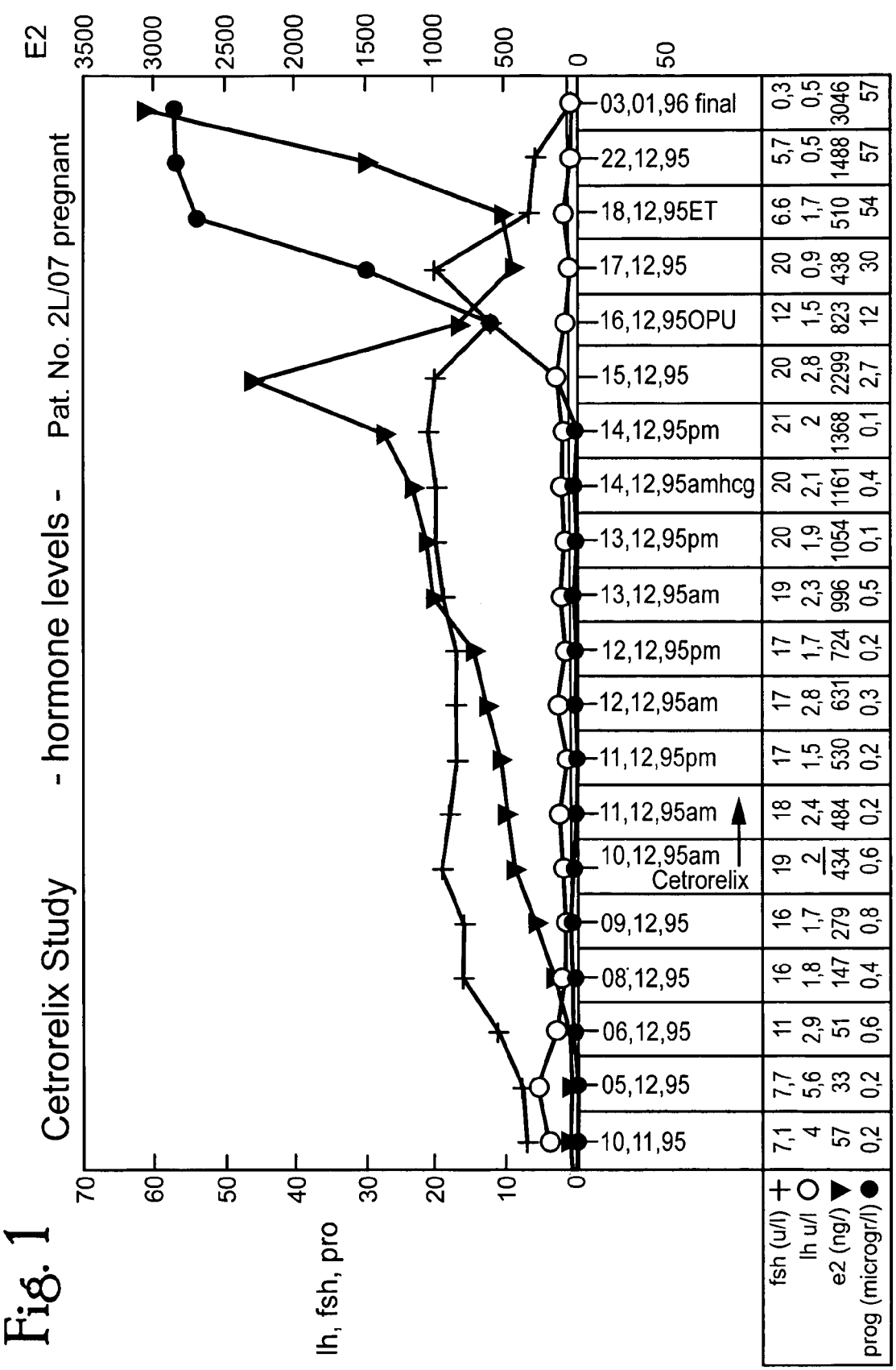
FIG. 1 shows monitoring of important reproductive hormones in a female patient (patient no. 2L/07) treated with subcutaneous injection of Cetrorelix Acetat-Lyophilisat. The hormone levels of luteinizing hormone (LH) (μg/l) (○), follicular stimulating hormone (FSH) (μg/l) (+), progesterone (μg/l) (●), and oestradiol ($E_2$) (ng/l) (▼) were measured in female patient number 21L07 at time intervals one month (Nov. 10, 1995) and four consecutive days before (Dec. 05, 1995-Dec. 09, 1995) a dual dose regimen of Cetrorelix (3 mg) was administered subcutaneously on Dec. 10, 1995 and Dec. 11, 1995. The patient's LH, FSH, progesterone and oestradiol levels were measured afterward between Dec. 11, 1995 and Dec. 14, 1995 wherein ovulation in the patient was induced with human chorionic gonadotrophin (HCG) on Dec. 14, 1995. The patients LH, FSH, progesterone, and oestradiol levels were also measured after HCG treatment through ovum pick up (OPU; Dec. 16, 1995), and embryo transfer (ET) on Dec. 14, 1995. Hormone levels were also measured on the 4th and (Dec. 22, 1995) and 16th day after ET(Jan. 3,1996).

238 patients were treated with Cetrorelix by subcutaneous injection of Cetrorelix Acetat-Lyophilisat.

134 patients were treated with multiple doses and 104 patients with single or dual doses. The multiple doses are 0.25 mg/day or higher. The single dose was 3 mg or higher. No premature LH surge was seen in any patient undergoing controlled ovarian superovulation for assisted reproduction technology (COS/ART) treated with these dosages. Multiple doses were applied for 3 to a maximum of 10 days dependent on follicular development.

As a result 71 pregnancies were obtained=30.0%

38 of 134 following the multiple does regimen=28.4%

33 of 104 following the single/dual dosage regimen=31.7%

Following treatment 44 babies were born that means 15 following multiple does and 29 following single/dual does. 16 pregnancies are still ongoing. FIG. 1 shows this in particular.

FIG. 1 shows an absolute prevention of any premature LH surge. Furthermore, FSH secretion is maintained at a natural level and therefore the individual estrogen development is not affected.

EXAMPLE 2

Combination of the GnRH antagonist Cetrorelix, clomifen citrate(CC) and gonadotrophins for hormonal stimulation for IVF/ICSI.

New controlled ovarian stimulation (COS) protocols become possible, which combine the advantages of clomifen citrate/gonadotrophin stimulation and pituitary suppression with Cetrorelix.

COS was started on day 2 after spontaneous menstrual bleeding using 100 mg CC per day for 5 or 7 days. The antagonist Cetrorelix (0.25 mg s.c.) was given starting on stimulation day 6 combined with either urinary hMG or recombinant FSH (3 ampoules/d) in a prospective randomized way.

After two days of gonadotrophin injection, the dose was individualized. Human chorionic gonadotropin was given for ovulation induction, if at least 3 follicles were ≧17 mm in diameter. In total, 30 patients were included in the study. 15 were randomized in each group. Intra cytoplasmatic sperm injection (ICSI) was applied in each case.

Results: A mean number of 24±4.7 and 23.4±7.0 ampoules hMG and recombinant FSH were used, respectively, 7.7±3.8 and 6.4±2.6 oocytes per cycle were retrieved, of which 74% and 80% were metaphase II oocytes. There were no differences regarding fertilization rates (42% vs. 53%), transfer rate/cycle (87% vs. 80%) and clinical pregnancy rate/transfer (4/14 vs. 1/11). No case of ovarian hyperstimulation syndrome (OHSS) was observed.

Conclusions: This method of COS yields a sufficient number of mature oocytes with a high pregnancy rate. Compared to the long protocol, this protocol is very convenient for the patient, the amount of gonadotropins is reduced, and no case of OHSS was observed. The hormone withdrawal symptoms as well as the problems of cyst formation were avoided, and the costs of therapy are reduced to an important degree.

What is claimed is:

1. A method of treating infertility disorders comprising administering an LHRH-antagonist selected from the group consisting of ganirelix, antarelix, antide, azaline B, ramorelix, A-76154, Nal-Glu, 88-88 and cetrorelix, and inducing follicle growth by administration of hMG or recombinant FSH (Controlled Ovarian Stimulation) in combination with clomiphene, wherein the administration of said LHRH-antagonist is sufficient to suppress endogenous LH while maintaining FSH secretion at a natural level and estrogen development is not affected until ovulation induction.

2. The method according to claim 1, wherein Controlled Ovarian Stimulation is started on day 2 after spontaneous menstrual bleeding by administering 100 mg clomiphene per day for 3 to 7 days and 0.2 to 1.0 mg cetrorelix is administered with hMG starting on stimulation day 5.

3. The method according to claim 1, wherein Controlled Ovarian Stimulation is started on day 2 after spontaneous menstrual bleeding by administering 100 mg clomiphene per day for 3 to 7 days and 0.2 to 1.0 mg cetrorelix is administered with recombinant FSH starting on stimulation day 6.

4. The method according to claim 3, wherein cetrorelix is administered subcutaneously in an amount between 0.1 and 5 mg per day during a multiple dosing regimen.

5. The method according to claim 1, wherein the LHRH antagonist is administered as a single or dual subcutaneous dose in an amount between 1 and 10 mg.

6. The method according to claim 5, wherein the LHRH antagonist is administered as a single or dual subcutaneous dose in an amount between 2 and 6 mg.

7. The method according to claim 1, wherein the LHRH antagonist is administered as an initial single dose in the range of 1 mg to 10 mg, followed by a multiple daily dose in an amount between 0.2 and 1.0 mg.

8. The method according to claim 7, wherein the single dose is between 2 and 6 mg.

9. The method according to claim 1, wherein ovulation is induced by administration of FSH or LH.

10. The method according to claim 1, wherein ovulation is induced by administration of LHRH or LHRH agonist.

11. The method according to claim 1, wherein ovulation is induced by human chorionic gonadotropin (HCG).

12. The method according to claim 1, wherein LHRH or an LHRH antagonist is administered so that luteal phase supplementation is avoided and negative effects of HCG are prevented during the luteal phase.

13. The method according to claim 1, wherein FSH, LH, LHRH, or LHRH agonist is administered so that ovarian hyperstimulation syndrome is avoided.

14. A method of treating infertility disorders comprising administering an amount of cetrorelix as an LHRH antagonist which is sufficient to suppress endogenous LH while maintaining FSH secretion at a natural level and not affecting estrogen development and further administering clomiphene to induce follicle growth, wherein after cessation of cetrorelix administration, subsequent follicle development is facilitated with remaining endogenous LH and FSH.

15. The method of claim 14, wherein cetrorelix is administered beginning on cycle day 6 to 10 and ovulation is induced between day 7 and day 11 of the menstrual cycle.

16. The method of claim 14, wherein cetrorelix is administered either in a single or dual dose of 1 to 10 mg or in a multiple dosage of 0.1 to 0.5 mg starting at cycle day 1 to 10 and ovulation is induced between day 9 and day 20 of the menstrual cycle.

17. The method according to claim 16, wherein cetrorelix is administered starting on cycle day 4 to 9.

18. A method of Controlled Ovarian Stimulation (COS) comprising administering an LHRH antagonist selected from the group consisting of ganirelix, antarelix, antide, azaline B, ramorelix, A-76154, Nal-Glu, 88-88 and cetrorelix, and inducing follicle growth by administration of hMG or FSH in combination with clomiphene, wherein the administration of said LHRH antagonist is sufficient to suppress endogenous LH while maintaining FSH secretion at a natural level and estrogen development is not affected until ovulation induction.

19. A method of Controlled Ovarian Stimulation comprising administering an amount of cetrorelix as an LHRH antagonist which is sufficient to suppress endogenous LH while maintaining FSH secretion at a natural level and not affecting estrogen development and further administering clomiphene to induce follicle growth, wherein after cessation of cetrorelix administration, subsequent follicle development and ovulation is facilitated by endogenous LH and FSH.

20. A method of treating fertility disorders treatable by controlled ovarian stimulation and assisted reproduction techniques, comprising
administering an LHRH antagonist selected from the group consisting of ganirelix, antarelix, antide, azaline B, ramorelix, A-76154, Nal-Glu, 88-88 and cetrorelix, and inducing follicle growth by administration of hMG or FSH (Controlled Ovarian Stimulation) in combination with clomiphene,
wherein the administration of said LHRH antagonist is sufficient to suppress endogenous LH while maintaining FSH secretion at a natural level and estrogen development is not affected until ovulation induction; and
performing assisted reproduction techniques following induction of ovulation.

21. A method of treating infertility disorders treatable by controlled ovarian stimulation and assisted reproduction techniques, comprising
administering an amount of cetrorelix as an LHRH antagonist which is sufficient to suppress endogenous LH while maintaining FSH secretion at a natural level and not affecting estrogen development and further administering clomiphene to induce follicle growth, wherein after cessation of cetrorelix administration, subsequent follicle development and ovulation is facilitated with remaining endogenous LH and FSH, and
performing assisted reproduction techniques following ovulation.

* * * * *

UNITED STATES PATENT AND TRADEMARK OFFICE
CERTIFICATE OF CORRECTION

| | | |
|---|---|---|
| PATENT NO. | : 7,393,834 B2 | Page 1 of 1 |
| APPLICATION NO. | : 10/661780 | |
| DATED | : July 1, 2008 | |
| INVENTOR(S) | : Philippe Bouchard et al. | |

It is certified that error appears in the above-identified patent and that said Letters Patent is hereby corrected as shown below:

Please add the following reference.

-- Stoeckemann et al., "Effects of the Luteinizing-hormone-releasing hormone (LHRH) antagonist ramorelix (hoe013) and the LHRH agonist buserelin or dimethylbenz [] anthrracene-induced mammary carcinoma: studies with slow-release formulation," J. Cancer Res. Clin. Oncol., Hoechst AG, Pharma-Research (Frankfurt/Main, Germany), Vol. 119 (No.8), p.457-462, (1993). --

Signed and Sealed this

Thirteenth Day of January, 2009

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,393,834 B2 | Page 1 of 1 |
| APPLICATION NO. | : 10/661780 | |
| DATED | : July 1, 2008 | |
| INVENTOR(S) | : Philippe Bouchard et al. | |

It is certified that error appears in the above-identified patent and that said Letters Patent is hereby corrected as shown below:

Item (56) Other Publications,

Please add the following reference.

-- Stoeckemann et al., "Effects of the Luteinizing-hormone-releasing hormone (LHRH) antagonist ramorelix (hoe013) and the LHRH agonist buserelin or dimethylbenz [] anthrracene-induced mammary carcinoma: studies with slow-release formulation," J. Cancer Res. Clin. Oncol., Hoechst AG, Pharma-Research (Frankfurt/Main, Germany), Vol. 119 (No.8), p.457-462, (1993). --

This certificate supersedes the Certificate of Correction issued January 13, 2009.

Signed and Sealed this

Third Day of February, 2009

JOHN DOLL
*Acting Director of the United States Patent and Trademark Office*